(12) United States Patent  
Sexton

(10) Patent No.: US 8,047,399 B1
(45) Date of Patent: Nov. 1, 2011

(54) DISPENSER FOR TRANSDERMAL DEVICES

(75) Inventor: Frederick A. Sexton, Rumson, NJ (US)

(73) Assignee: Purdue Pharma L.P., Stamford, CT (US)

( * ) Notice: Subject to any disclaimer, the term of this patent is extended or adjusted under 35 U.S.C. 154(b) by 610 days.

(21) Appl. No.: 12/167,966

(22) Filed: Jul. 3, 2008

Related U.S. Application Data

(60) Provisional application No. 60/948,159, filed on Jul. 5, 2007.

(51) Int. Cl.
*G07F 11/00* (2006.01)
(52) U.S. Cl. ............ 221/2; 221/155; 221/156; 221/174; 206/440; 604/20
(58) Field of Classification Search .................... 604/20; 221/2, 155, 156, 174; 206/440
See application file for complete search history.

(56) References Cited

U.S. PATENT DOCUMENTS

| | | |
|---|---|---|
| 4,314,554 A | 2/1982 | Greatbatch |
| 5,306,235 A | 4/1994 | Haynes |
| 5,697,896 A | 12/1997 | McNichols et al. |
| 5,697,946 A | 12/1997 | Hopper et al. |
| 5,885,211 A | 3/1999 | Eppstein et al. |
| 5,978,701 A | 11/1999 | Johnson et al. |
| 5,983,130 A | 11/1999 | Phipps et al. |
| 6,035,234 A | 3/2000 | Riddle |
| 6,086,572 A | 7/2000 | Johnson et al. |
| 6,136,839 A | 10/2000 | Isakson et al. |
| 6,148,232 A | 11/2000 | Avrahami |
| 6,611,706 B2 | 8/2003 | Avrahami et al. |
| 6,662,044 B2 | 12/2003 | Crawford et al. |
| 6,748,266 B2 | 6/2004 | Bernabei |
| 6,796,429 B2 * | 9/2004 | Cameron et al. .............. 206/440 |
| 7,010,343 B2 | 3/2006 | Bernabei |
| 7,141,034 B2 | 11/2006 | Eppstein et al. |
| 7,392,080 B2 | 6/2008 | Eppstein et al. |
| 7,537,590 B2 | 5/2009 | Santini et al. |
| 2008/0208107 A1 | 8/2008 | McRae et al. |
| 2008/0234628 A1 * | 9/2008 | Dent et al. ....................... 604/20 |

OTHER PUBLICATIONS

Paul A. Insel, "Analgesic-Antipyretic and Antiflammatory Agents and Drugs Employed in the Treatment of Gout" in *Goodman & Gilman's The Pharmacological Basis of Therapeutics* (Perry B. Molinhoff and Raymond W. Ruddon eds., 9th ed 1996), pp. 617-657.

(Continued)

*Primary Examiner* — Kevin C Sirmons
*Assistant Examiner* — Emily Schmidt
(74) *Attorney, Agent, or Firm* — Leason Ellis LLP

(57) ABSTRACT

A dispenser places transdermal devices and packaged transdermal devices in an electrically charged state. The dispenser is particularly suitable for transdermal devices that include electrically actuatable components, such as transdermal, drug-delivery patches that include microporator circuitry. A controller can be operatively coupled to a power circuit of the dispenser to control the times that transdermal devices can be charged, thereby providing a measure of control over use and misuse of the transdermal devices to be dispensed.

10 Claims, 6 Drawing Sheets

OTHER PUBLICATIONS

Glen R. Hanson, "Analgesic, Antipyretic and Anti-Inflammatory Drugs" in *Remington: The Science and Practice of Pharmacy*, vol. II 1196-1221 (A.R. Gennao ed., 19th ed. 1995), pp. 1196-1221.

T.A. Peterson et al., "Design, Development, Manufacturing and Testing of Transdermal Drug. Delivery Systems" in *Transdermal and Topical Drug Delivery Systems* (T.K. Ghosh et al. eds., 1997) pp. 249-297.

U.S. Appl. No. 12/130,410, Frederick Sexton: "Transdermal Patch", filed May 30, 2008, pending.

U.S. Appl. No. 12/130,496, Frederick Sexton "Transdermal Device Having Mechanical Assist for Porator-To-Skin Contact", filed May 30, 2008.

U.S. Appl. No. 12/131,458, Frederick Sexton "Switch for Transdermal Patch", filed May 30, 2008, pending.

U.S. Appl. No. 12/131,508 Frederick Sexton "Transdermal Patch Packaging", filed Jun. 2, 2008, pending.

\* cited by examiner

DISPENSER FOR TRANSDERMAL DEVICES

CROSS REFERENCE TO RELATED APPLICATIONS

This application claims the benefit of priority, under 35 U.S.C. §119(e), of U.S. Provisional Application Ser. No. 60/948,159, filed Jul. 5, 2007, which is hereby incorporated by reference in its entirety.

FIELD OF THE INVENTION

This invention relates to dispensers that impart a potential voltage to packaged or loose transdermal devices, which voltage can be used to store a charge on-board the transdermal device and to methods concerning same.

BACKGROUND OF THE INVENTION

Transdermal drug delivery and monitoring systems are desirable in many circumstances in that self-administration by untrained persons is required. For example, transdermal drug patches are available commercially for curbing nicotine cravings due to smoking, as a birth-control aid, and a wide variety of specific applications. A principal benefit of transdermal drug delivery as compared to the historical use of injectable dosage forms is that it provides the drug directly to the blood stream without the discomfort of needles, lancets and other sharp instruments, and without the need for training in the use and disposal of such instruments. As compared to oral dosage forms, transdermal delivery can be more effective for some regimens when it is desirable to deliver a drug clear of the hostile environment presented by gastrointestinal juices or by first pass metabolism. Further, transdermal devices permit monitoring of blood components.

It is generally desirable to enhance transdermal drug delivery and blood monitoring, and in this regard there are several known methods for increasing the permeability of skin to drugs. Among these is a methodology known as "microporation" or "poration", which refers to the formation of a hole or crevice (defined herein as a "micropore") in a biological membrane, such as skin or mucous membrane, of a patient. The micropore lessens the barrier properties of the skin to the passage of drugs into the patient for a therapeutic treatment, or of biological fluids out of the patient for analysis. The micropore can be range from about 1 to about 1000 microns in diameter and typically extends into the skin sufficiently so as to reduce the barrier properties of the stratum corneum without adversely affecting the underlying tissues. Typically, multiple micropores are created in a single application of this methodology. See, for example, U.S. Pat. Nos. 5,885,211 and 7,141,034 (the '034 patent) for a description of various thermal and electrical microporation techniques and devices.

In order to create micropores, energy is applied to the skin surface. In the '034 patent, that energy is provided either by a hand-held external device or from a self-contained unit that combines a transdermal delivery device with an energy source. The devices proposed by the '034 patent are multi-part assemblies, which appear to be cumbersome and awkward to use. It would be preferable to have a light-weight, flexible transdermal device that is electrically chargeable and fully disposable as compared to the assemblies described in the '034 patent. Alternatively, there are disposable transdermal patches with chemical reservoirs that can be mixed together to create an exothermal reaction, which might be made suitable for creating a micropore; however, the chemicals required and their associated reactions introduce substantial complexities into the manufacture of the transdermal device.

Accordingly, there remains a need for improved methods and devices for transdermal delivery of agents such as drugs and monitoring of analytes such as blood components, as well as packaging for such devices. The present invention concerns dispensers adapted to place transdermal devices of this nature in a charged state in which they are "ready to microporate" or ready to perform another function that utilizes an electric potential.

SUMMARY OF THE INVENTION

The invention provides, in a first aspect that stands apart from other aspects, a dispenser configured to dispense a transdermal device such as a transdermal patch in an electrically charged state. The dispenser includes a housing having a well sized to receive the transdermal device; a pair of electrodes spaced from one another and having a first position in which the electrodes are clear of contact with the transdermal device and a second position in which the electrodes engage any transdermal device seated in the well, a power circuit electrically connectable to the electrodes to apply a voltage thereacross, and a switch electrically interposed between at least one of the electrodes and the power circuit. The switch is operative to selectively apply the voltage from the power circuit across the electrodes to thereby place the transdermal device in the electrically charged state.

A dispenser in accordance with the foregoing can further include a cover which is movably mounted relative to the housing. The electrodes can be supported by the cover so that the electrodes engage the transdermal device and wherein the cover has an open position providing access to the well and placing the electrodes in the first position and a closed position providing the voltage to any transdermal device in the well and placing the electrodes in the second position.

The invention also provides, in another aspect that stands apart from the first aspect, a dispenser configured to dispense a transdermal device such as a transdermal patch in an electrically charged state in which there is again a housing having a well sized to receive the transdermal device, a pair of electrodes extending into the well and below any transdermal device seated therein, a power circuit electrically connectable to the electrodes to apply a voltage thereacross, and a switch electrically interposed between at least one of the electrodes and the power circuit and operative to selectively apply the voltage from the power circuit across the electrodes to thereby place the transdermal device in the electrically charged state, but in which the electrodes are stationarily mounted. In accordance with this aspect of the invention, a bearing surface moves between a first position that is clear of any transdermal device in the well and a second position in which the bearing surface presses upon the transdermal device to cause electrical engagement of the electrodes with the transdermal device.

A dispenser in accordance with any of the foregoing aspects also can further include a controller operatively connected so as to preclude a voltage across the electrodes for a time period after dispensing the transdermal device in the electrically charged state.

The invention also provides, in a further aspect that stands apart from the previous aspects, a transdermal patch can be dispensed in an electrically charged state while contained within a sealed package. In this aspect of the invention, the transdermal patch has first and second contacts in respective conductive contact with first and second conductive traces on a surrounding packaging member. The surrounding packaging members sealingly engage each other to define a storage region therebetween that contains the transdermal patch. The dispenser engages a portion of the first and second conductive traces through the packaging at a location clear of the storage region. The conductive traces are contactable so as to transfer an electrical potential from the dispenser electrodes along the conductive traces and over to the first and second contacts of the transdermal patch.

A dispenser in accordance with any of the foregoing aspects also can further include a controller operatively connected so as to preclude a voltage across the electrodes for a time period after dispensing the transdermal device in the electrically charged state.

In a specific application of the invention, the transdermal patch contains a drug for transdermal delivery and a porator circuit adapted to create micropores in the skin of a user of the patch. An energy storage device on-board the patch has first and second terminals that extend to first and second electrical contacts, respectively. The dispenser includes electrodes that establish electrical connection to the first and second contacts, directly or indirectly, and thereby impart a voltage to bring the energy storage device to an electrically charged state. The transdermal patch can be separated from the dispenser, removed from any surrounding packaging, applied to skin, and thereafter have the stored charge discharged to effect microporation of the skin of the user of the patch.

Packaged transdermal devices, and refills that comprise a series of packaged transdermal devices, can be configured so as to cooperate with the dispenser so as to be dispensable in an electrically charged state.

These and other aspects, features and advantages will be apparent from the following description of certain embodiments of the invention which is to be read in conjunction with the accompanying drawing figures which illustrate such embodiments.

BRIEF DESCRIPTION OF THE DRAWING FIGURES

DETAILED DESCRIPTION OF CERTAIN EMBODIMENTS OF THE INVENTION

The present invention concerns a dispenser that is configured to impart a potential voltage to a transdermal device, including transdermal devices that are sealed within surrounding packaging, prior to use by a user. The potential voltage charges an on-board energy storage device to provide power to the transdermal device that remains available, free of external connection to a power source, after the transdermal device has been separated from the dispenser and any surrounding packaging and then attached to the skin of a user.

In a preferred mode, the transdermal device is a transdermal patch that includes a reservoir or a matrix to serve as a source for a drug, such as an opiate or other analgesic agent, as well as on-board circuitry suitable for microporating the skin of a user once adhered to the user's skin. Several suitable constructions for a patch are described in co-pending U.S. Provisional Application Ser. No. 60/941,246, filed on May 31, 2007, entitled "Transdermal Patch," which is hereby incorporated by reference in its entirety. Such a transdermal device can be placed in a charged, "ready-to-microporate" state within the dispenser and remain in that state for convenient mounting to the skin until actuated. After any surrounding packaging has been opened and discarded, and after the patch has been mounted on the skin, the microporation circuitry can be activated to release the stored energy, drive the microporator, and thereby create micropores in the skin in preparation for drug delivery from the drug reservoir or drug matrix portion of the patch.

Figure 1:
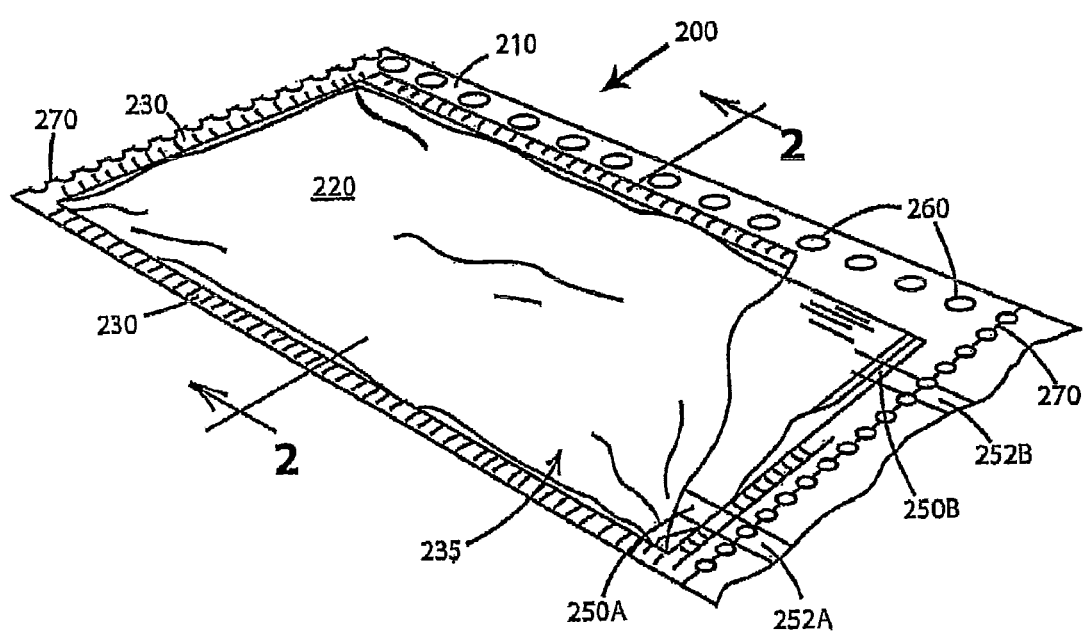
FIG. 1 is a top perspective view, partially broken away, of an exemplary packaged transdermal delivery device suitable for use in connection with various embodiments of the invention.

FIG. 1 illustrates a patch 100 of the type including actuatable circuitry (e.g., microporator circuitry) sealed within a surrounding package 200. The package 200 defines a cavity or sealed storage region between first and second foil members 210, 220. Either or both of the foil members can comprise a laminate of two or more plies of material, such as a water-impermeable metal foil layer and a non-conductive layer. The foil members are engaged at peripheral region 230, such as by crimping, heat-welding, adhesives, or a combination of these techniques, to define a sealed storage region 235 for storing the patch 100. Also within the storage region 235 are first and second conductive traces 250A, 250B, insulatively spaced from one another, which can carry a voltage potential or a current to the patch 100. The conductive traces 250A, 250B are in electrical contact with respective portions 252A, 252B that extend exteriorly of the storage region 235. The portions 252A, 252B permit electrical contact with an external power source while the patch remains sealed and, more preferably, hermetically sealed, within the storage region 235. Packaging of this construction is further described in co-pending U.S. Provisional Application Ser. No. 60/941,157, filed on May 31, 2007, entitled "Transdermal Patch Packaging," which is hereby incorporated by reference in its entirety. More generally, when the discussion permits, the conductive traces 250A, 250B and conductive portions 252A, 252B are referred to as conductive traces 250A, 250B and conductive portions 252A, 252B, respectively.

Figure 2:
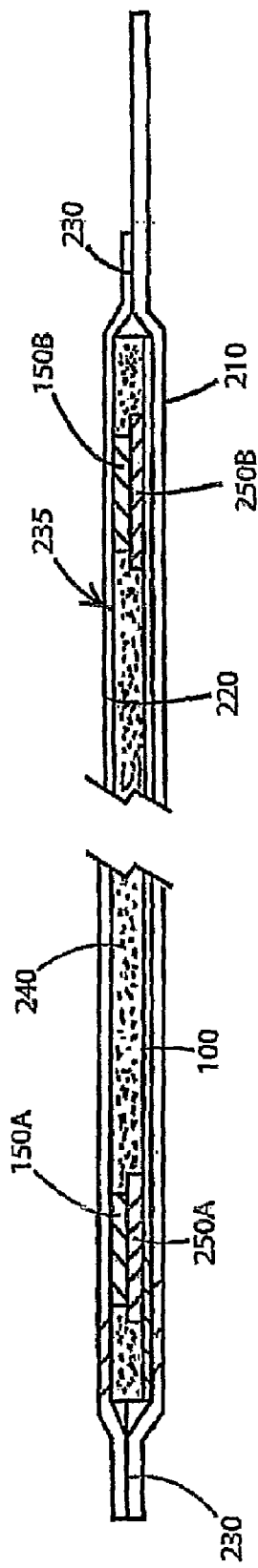
FIG. 2 is a cross-sectional view taken along line 2-2 of FIG. 1.

FIG. 2 illustrates in cross section the transdermal patch 100 seated within the storage region 235 of the package, and shows an optional adhesive 240 that can be used to secure the patch in a desired orientation within the storage region. As shown in FIG. 2, the patch includes a pair of electrical contacts 150A, 150B that are oriented so as to make respective conductive contact with the conductive traces 250A, 250B. In this orientation, the contacts 150A, 150B convey any potential gradient or current applied across the conductive traces 250A, 250B to circuitry on-board the patch, such as the microporation circuitry described in the aforementioned U.S. Provisional Application Ser. No. 60/941,246.

Figure 3:
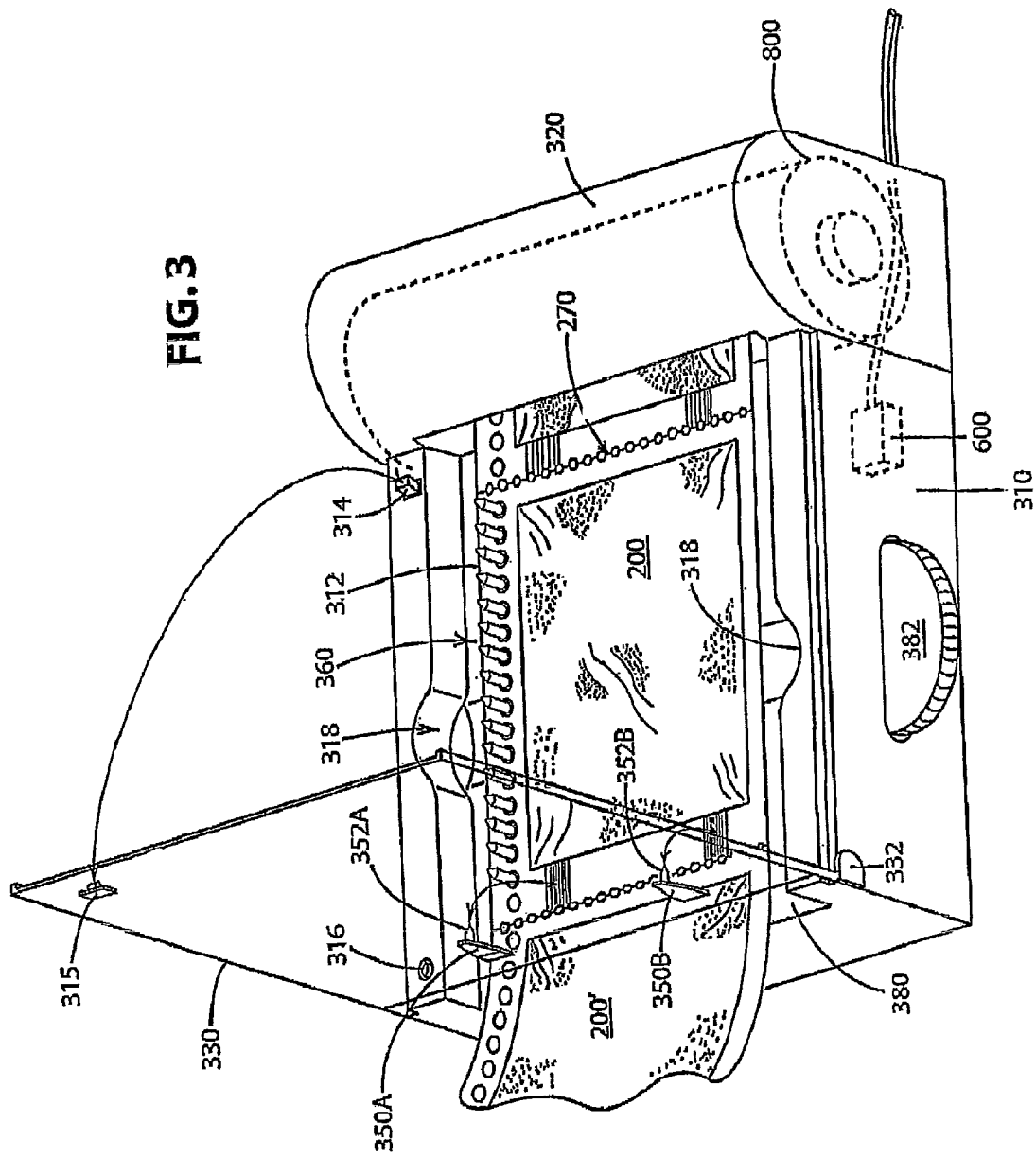
FIG. 3 is a top perspective view of a first embodiment of a dispenser in accordance with the invention.

With reference now to FIG. 3, a dispenser 300 in accordance with a first embodiment of the invention is illustrated.

The dispenser generally comprises a housing 310 having a well 312 sized to receive and position the package 200, electrodes 350A, 350B, and a power circuit 600 that applies a voltage potential across or a current through the electrodes 350A, 350B.

A package 200 disposed in the well 312 is engaged by the electrodes 350A, 350B so that the electrodes make electric contact with the conductive portions 252A, 252B, respectively, while the transdermal device within the packaging remains sealed. More particularly, piercing tips 352A, 352B at the ends of electrodes 350A, 350B make piercing contact through any layers of the foil members 210, 210 with the conductive portions 252A, 252B. The conductive portions convey the potential voltage or current along the conductive traces 250A, 250B to the contacts 150A, 150B of the patch 100. The contacts 150A, 150B connect the energy storage device of the patch 100 as a load on the power circuit 600. Once electrical contact is established by the electrodes 350, a voltage potential or a current is conveyed to the energy storage device on-board the transdermal device to charge the on-board energy storage device. As a result, the transdermal device can be removed from the dispenser, unpackaged, and have its components electrically actuated free of any external connections. As above, when the discussion permits, the electrodes 350A, 350B and piercing tips 352A, 352B are more generally referred to electrodes 350 and piercing tips 352, respectively.

Figure 6:
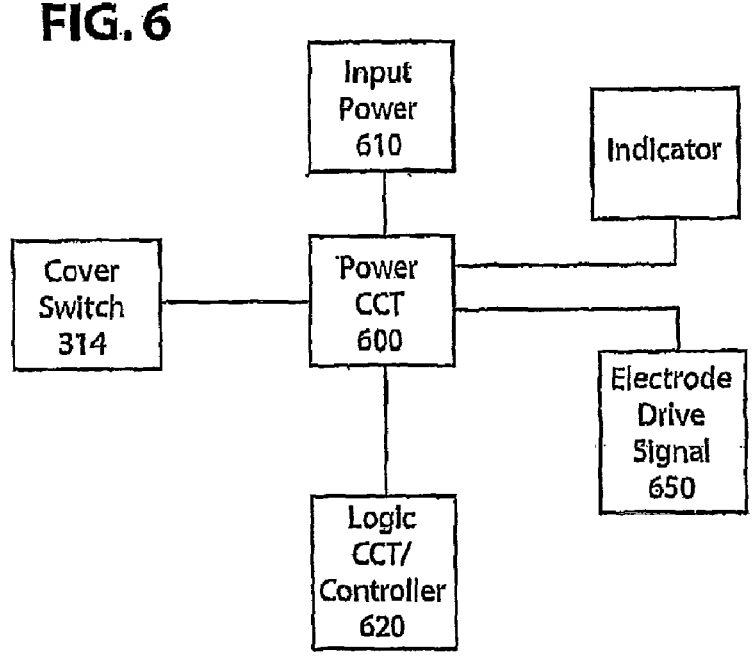
FIG. 6 is a schematic illustration of a circuit arrangement useful with the embodiments of FIGS. 3 and 4.

Referring now to FIGS. 3 and 6, the housing 310 preferably includes one or more switches that permit a voltage to appear across the electrodes 350 or a current to flow through the electrodes while in a closed position. A switch 314 can be positioned to respond to closure of a protective cover 330 so as to enable the power circuit 600 to deliver an electrode drive signal 650 to the electrodes only when the cover is in the closed position. A corresponding feature 315 on the cover cooperates with the switch to change its state in response to closure or opening of the cover. A switch can be disposed elsewhere on the housing to prevent or allow the electrode drive signal to drive the electrodes 350, and can be in addition to the switch 314 or instead of switch 314. The power circuit operates to selectively output a drive signal to energize the electrodes and thereby charge an energy storage device included within the packaging seated in the well 312 of the housing. The drive signal can be a voltage in the range of about 1 to about 12 volts D.C, and is selected so as to provide an energy source that is matched to the requirements of the transdermal devices that are seated within the housing, with or without surrounding packaging. At least one switch is electrically interposed between at least one of the electrodes and the power circuit and operative within the power circuit to selectively apply the voltage from the power circuit across the electrodes or to selectively permit a current to flow through the electrodes and thereby place the transdermal patch in the electrically charged state. The power circuit receives input power 610, which can be from a battery supply or converted from an AC connection to mains. The housing also can include at least one indicator 316, which is driven by the power circuit 600, to indicate whether a load is properly connected across the electrodes 350A, 350B (that is, to indicate that a current is being drawn), whether the load continues to be drawing current (e.g., to indicate that the energy storage device is not fully charged), or both. A single indicator can light up initially when a load starts to be drawn to indicate proper seating of the package 200 and can remain lit until the energy storage device is fully charged at which time the device 100 within the package stops loading the power circuit.

In the embodiment of FIG. 3, the electrodes 350 are mounted to the protective cover 330. The cover is moveably mounted relative to the housing 310 so as to move between open (as shown) and closed positions. For example, the cover can be hingedly mounted to the housing by a hinge 332. The electrodes are spaced from one another and move between a first position in which the electrodes are clear of contact with the package 200 and a second position in which the electrodes engage any package seated in the well. The first position corresponds to the cover-open position and the second position corresponds to the cover-closed position. When the cover is in the open position, a user has access to the well 312, and can position or remove a package 200, optionally by reaching under the patch using finger purchases 318 that communicate with the well 312. When the cover is in the closed position, the piercing tips 352A, 352B engage the conductive portions 252A, 252B, respectively, which extend outside of the sealed storage region 235, to impart a voltage or a current to any package seated in the well.

To ensure that the conductive portions 252A, 252B are in alignment with respective piercing tips 352A, 352B, the conductive portions can have dimensions that accommodate any tolerance differences between the shape of the well 312 and the shape of the package 200. Preferably, however, the package includes a feature such as sprocket holes 260 (see FIG. 1) that mate with corresponding guides 360 that positively ensure alignment of the conductive portions 252 with the piercing tips 352. The guides 360 can assume a variety of forms, such as posts that are received within the sprocket holes 260. By seating the package 200 in the well 312 and concurrently aligning the sprocket holes 260 over and around the guides 360, the conductive portions 252 of the package are affirmatively brought into alignment with the electrode tips 352. The indicator 316, if provided, confirms proper placement of the package within the dispenser 300.

The dispenser 300 includes further features that operate to dispense packages 200 that are serially provided to the well 312 from a supply 320. As described below, the supply can store refills that contain multiple packages 200, each containing a patch. A series of packages can comprise an interconnected web with individual packages being severable from one another along transverse lines. Perforations 270 can be provided, for example, to ensure that the packages separate in regions clear of the adjacent sealed storage regions 235. Packages 200 can be serially dispensed from the well 312, after transferring charge to energy storage device(s) on transdermal devices within each package, by advancing the package from the supply 320 to an outlet 380 on an opposite side of the dispenser. Packages 200 can be advanced from the supply to the outlet by a conveyor mechanism which, as illustrated, can comprise a thumbwheel 382 or other manual or automated mechanism which is coupled to the guides 360 to cause them to scroll toward the outlet while simultaneously advancing one package 200 into the well and another package 200' from the well and out the outlet for use by the user. Preferably, the conveyor mechanism has a stop position so that packages are advanced the same distance each time the conveyor is utilized.

The conveyor mechanism operates to seat the package 200 in a position in which the electrodes 353 engage the package so as to store energy therein, for example, when the cover closes switch 314 and/or when any other switch in the power circuit is closed to complete the electrode drive circuit. The package 200' which has been ejected from the dispenser will have undergone a charging cycle in response to the electrodes 352 having engaged the conductive portions 252. Moreover, the package 200' is ready for separation from the dispenser, removal of the packaging, adhering to the skin of the user, and actuation of the microporator circuitry (or other circuitry that can be electrically actuated using the energy that has been imparted by the dispenser and stored on-board the patch 100 within the package 200').

Figure 4:
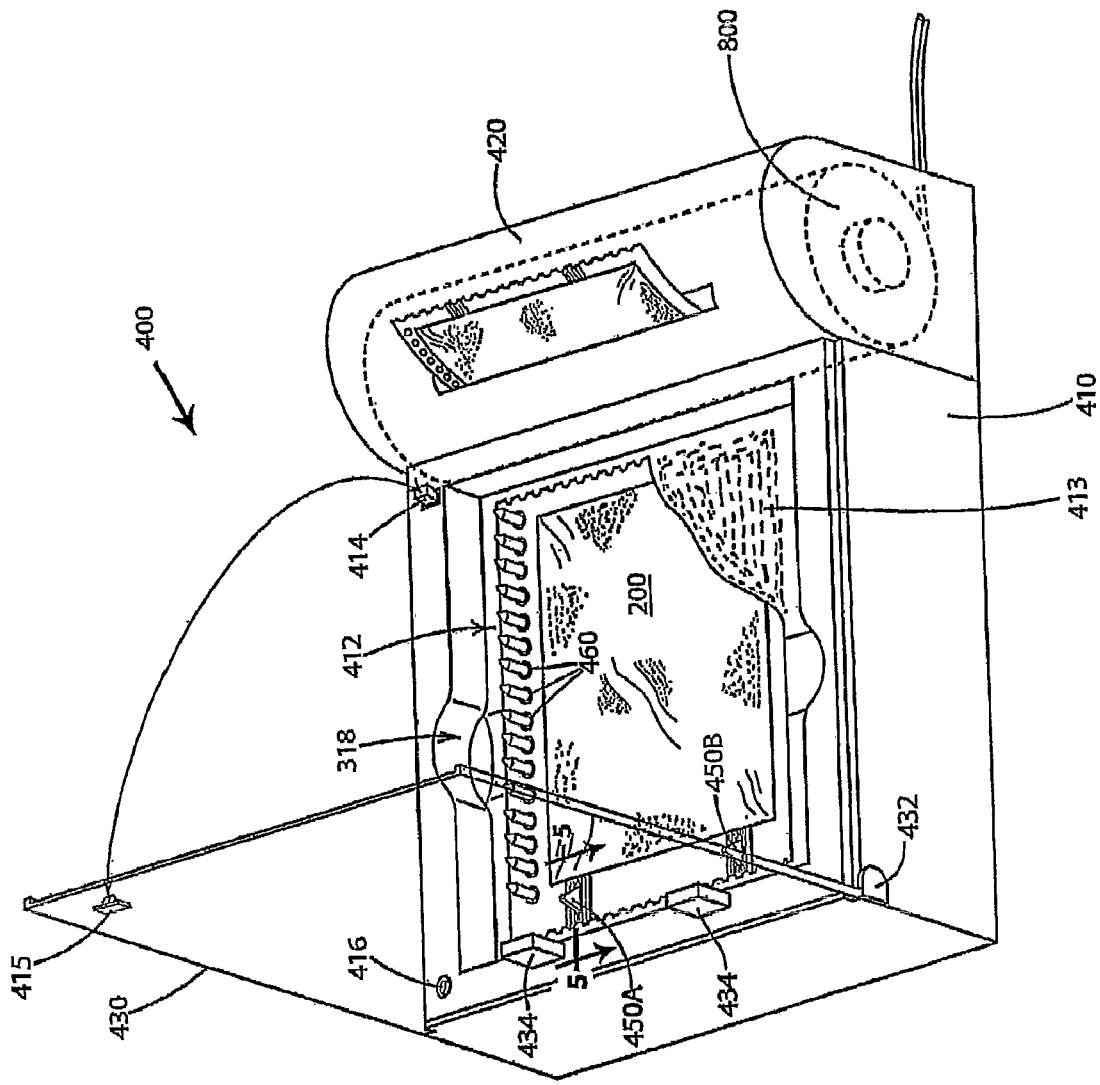
FIG. 4 is a top perspective view of a second embodiment of a dispenser in accordance with the invention.

With reference now to FIG. 4, a dispenser 400 constructed in accordance with a second embodiment of the invention is illustrated, in which reference numerals similar to those of the first embodiment refer to like elements. The dispenser 400 generally comprises a housing 410 having a well 412 sized to receive and position the package 200, electrodes 450A, 450B, and a power circuit 600 that applies a voltage potential across or a current through the electrodes 450A, 450B. As in the first embodiment, a package 200 disposed in the well 412 is engaged by the electrodes 450A, 450B so that the electrodes make electric contact with the conductive portions 252A, 252B, respectively, while the transdermal device within the packaging remains sealed. A switch 414 can be positioned to respond closure of a protective cover 430 having a corresponding feature 415 so as to enable the power circuit 600 to deliver an electrode drive signal 650 to the electrodes only when the cover is in the closed position. The housing can include at least one indicator 416, as previously described.

In the embodiment of FIG. 4, the electrodes 450 are mounted stationary within the well 412 and have piercing tips 452 extending above a flexible pad 413 that lines the bottom of the well. A user places a package 200 in the well 412, upon the flexible pad 413, so as to overlie the electrodes when so-placed in the well. Optionally, a supply 420 can be affixed to the dispenser 400, and, if provided, can contain a refill 800 having a set or series of packages for use by the user. Guides 460 can be provided to positively ensure alignment of the conductive portions 252 associated with each package introduced into the well with the piercing tips 452. As in the previous embodiment, the guides can assume a variety of forms, such as posts that are received within the sprocket holes 260.

Figure 5:
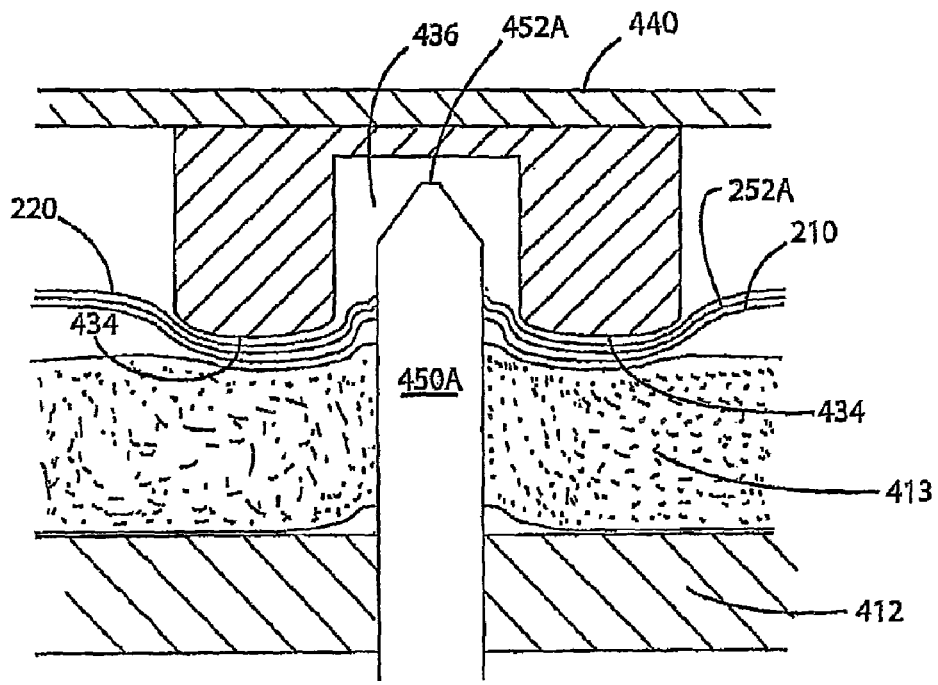
FIG. 5 is a detail view taken along line 5-5 of FIG. 4 of the second embodiment while the cover is in a closed position.

Engagement of the piercing tips of the electrodes with the conductive portions 252 again can be in response to movement of the cover 430. In the embodiment of FIG. 4, the cover includes one or more bearing surfaces 434 that bear down upon the transdermal patch at a location proximate to the electrodes 450 and cause the piercing tips 452 (see FIG. 5) to electrically engage respective conductive portions 252 associated with the package 200. When the cover is in an open position, the bearing surface 434 are in a first position clear of any transdermal patch in the well 412. When the cover is brought to the closed position, as shown in FIG. 5, the bearing surface 434 presses down upon the packaging 200 and the pad 413 yields to the pressing force. The cover can rotate about a hinge 432 (shown in FIG. 4), and the bearing surfaces 434 can be coupled to the cover such as when the cover and bearing surfaces are integral with one another. In response to the pressure applied by the bearing surface 434, the piercing tips 452 puncture and pass through the packaging (also shown in FIG. 4) and thereby make electrical contact with the conductive portions 252 (only portion 252A is shown in the detail of FIG. 5). The bearing surfaces optionally are part of a structure that includes a slot or cavity 436 that receives and contains the piercing tips 452.

In the embodiment of FIG. 3 in which a series of transdermal packages are interconnected along a web and coupled to and advanced through the dispenser 300, it is possible that the set of packages along the web can have their respective conductive traces 250A, 250B commonly held at a prescribed voltage provided by a dispenser so as to charge the energy storage devices associated with respective devices within the multiple packages 200, all at the same time. However, in some applications it may be preferable to supply a voltage or current to only one package and to not charge another package for a set period of time.

Figure 7:
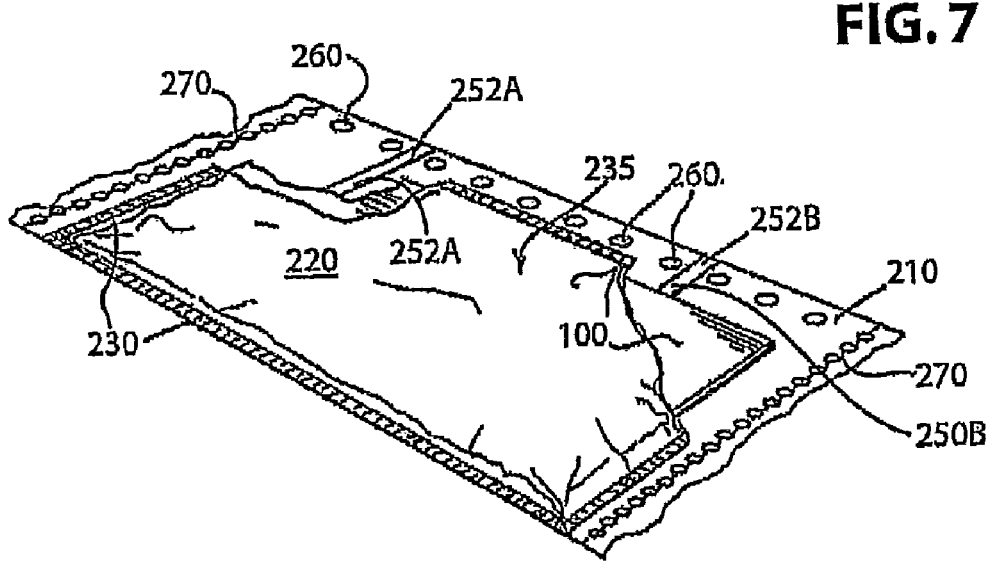
FIG. 7 is a top perspective view, partially broken away, of another exemplary packaged transdermal delivery device that is suitable for use in connection with various embodiments of the invention.

With reference again to FIG. 1, the package has conductive traces 250A, 250B that can extend in an uninterrupted, electrically continuous manner via conductive portions 252A, 252B so as to make contact with the conductive portions of the next package 200', and so on. Instead, the conductive traces can be arranged to be discontinuous from package to package so that the conductive traces of one package are not in electrical contact with the conductive traces of a next package that may be upstream or downstream along the webbing. In one embodiment, the package can have the conductive portions 252A, 252B terminate short of the periphery of the foil members 210, 220. In another embodiment, as illustrated in FIG. 7, the conductive traces and conductive portions can be arranged so as to extend non-parallel with the direction of the series of packages (e.g., instead be parallel to the perforations 270). In each of these variations the conductive traces 250A, 250B still make conductive contact with contacts 150A, 150B of any device contained within the storage region 235. The advantage of not having conductive traces of one package in electrical contact with the traces of a next package is that each package can be individually and preferably serially connected to a source of voltage or current within the dispenser so that only one package at a time is in a charged state and hence "ready-to-microporate" or perform some other function that requires electrical actuation.

However, in order to provide better control over the usage or misusage of packaged transdermal devices, the power circuit 600 can further include a logic circuit or controller 620 that is operatively connected to preclude a voltage appearing across the electrodes 350, 450 (see FIGS. 3 and 4) for a time period after having dispensed a package 200 in an electrically charged state. The logic circuit can comprise a timer combined with logic gates, or a processor that can measure the passage of time and enable the delivery of electrode drive signals 650 only after a set condition has been satisfied. The condition can be established by a pharmacist or doctor using administrative keys as understood by persons of skill in the software arts. The logic circuit or controller 620 can thus provide a control to prevent abuse of a prescribed regimen, such as to administer a transdermal patch twice daily by placing packages in the charged state only once until the a prescribed time period has elapsed since charging or removal of a prior package, or by providing one or more time windows during a day in which a package or patch can be charged.

Figure 8:
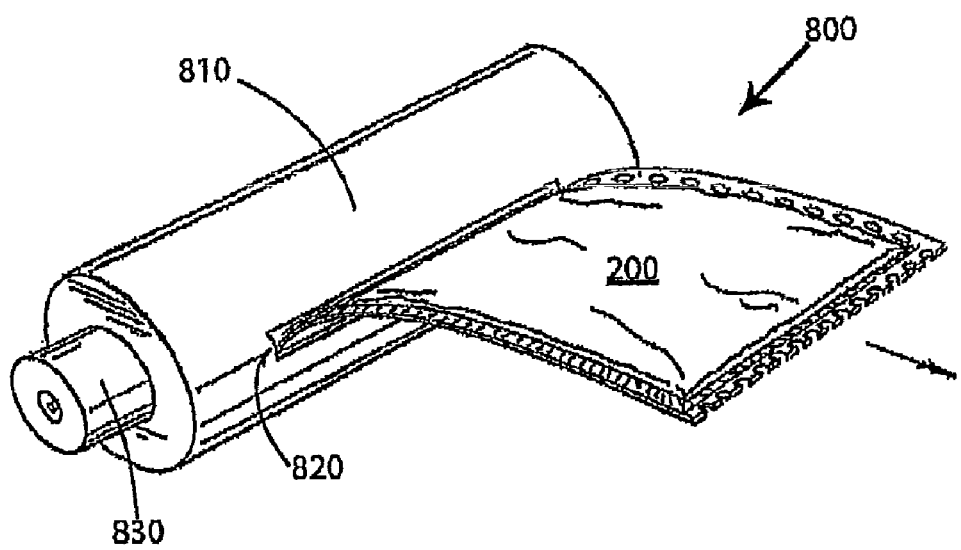
FIG. 8 is a perspective view of a refill housing that includes packaged transdermal delivery devices suitable for use in connection with various embodiments of the invention.

FIG. 8 illustrates a set of packaged transdermal devices 200 in the form of a refill 800. A series of packages 200, as previously described, are separable along perforations such as perforations 270, and are disposed within a refill housing 810. The packages 200 are serially retrievable from a slot 820 in the housing. Preferably, the slot 820 is sized and shaped to guide the packages outward. Optionally, the housing 810 can convey the electrode drive signal 650 to a package 200 prior to its being separated from the refill housing, by having conductive traces coupling the electrode drive signals to an interior of the housing and providing those signals to the conductive portions 252. However, it is presently preferred that the charging of energy storage devices within the packages 200 occur within the wells 312, 412 described above. The refill housing 810 provides a simple mechanism for a user to have a supply of packages adjacent or within a dispenser constructed in accordance with the invention. Preferably, the refill housing that encapsulates the packages includes a feature such as a spindle 830 suitable for mounting the refill in a single orientation within the dispenser.

In the foregoing discussion, packages 200 have been positioned within the dispenser, and more specifically within the wells 312, 412 of the embodiments discussed above. However, a dispenser in accordance with the invention can be used with an unpackaged transdermal device, such as the patch 100, if desired. In this mode of operation, the patch can include features that better ensure proper orientation of the electrodes 350, 450 and the contacts 150A, 150B on the patch such as labels, sprocket holes, or abutments that aid in the manual positioning of the patch within the well.

Also, in the foregoing description the dispenser has been described as having a well for holding a package 200 or patch 100, but the term "well" is to be broadly understood as a station adapted to receive a package or patch, and preferably arranged to ensure affirmative electrical contact with the package or patch, respectively.

In the foregoing description, certain features have been described in relation to certain embodiments of the invention, but these same features are to be understood as being useable in other arrangements and embodiments. For instance, the pad 413 can be used in the embodiment of FIG. 3. Accordingly, the invention is defined by the recitations in the claims appended hereto and equivalents thereof, and is not limited to particular details of any of the foregoing embodiments that rather are provided to facilitate an understanding of the invention and to satisfy certain statutory requirements.

I claim:

1. A dispenser configured to dispense a transdermal patch in an electrically charged state for microporation of skin of a user of the transdermal patch, comprising:
   a housing having a well sized to receive the transdermal patch;
   a pair of electrodes extending into the well and below any transdermal patch seated therein;
   a power circuit electrically connectable to the electrodes to apply a voltage thereacross;
   a switch electrically interposed between at least one of the electrodes and the power circuit and operative to selectively apply the voltage from the power circuit across the electrodes to thereby place the transdermal patch in the electrically charged state while received in the well; and
   a bearing surface having a first position clear of any transdermal patch in the well and a second position that bears down upon the transdermal patch at a location proximate to the electrodes so as to electrically engage the electrodes with the transdermal patch,
   whereby the transdermal patch is separable from the dispenser in the electrically charged state prior to use by the user and configured to effect microporation of the skin of the user of the transdermal patch by discharge from the electrically charged state.

2. The dispenser as in claim 1, further comprising a cover coupled to the bearing surface, the cover overlying the well when the bearing surface is in the second position.

3. The dispenser as in claim 1, wherein the cover is hingedly mounted.

4. The dispenser as in claim 1, further comprising an indicator connected to the power circuit so as to be responsive to the engagement of the electrodes with any transdermal patch in the well.

5. The dispenser as in claim 1, further comprising a finger purchase in the housing in communication with the well to ease removal of any transdermal patch from the housing.

6. The dispenser as in claim 1, further comprising a guide associated with the housing to orient the transdermal patch within the well.

7. The dispenser as in claim 1, wherein the electrodes have a piercing tip suitable for electrically engaging a conductive trace associated with a package surrounding any transdermal patch in the well.

8. The dispenser as in claim 1, further comprising a controller operatively connected so as to preclude a voltage across the electrodes for a time period after dispensing the transdermal patch in the electrically charged state.

9. The dispenser as in claim 1, further comprising a supply of transdermal patches coupled to the housing and serially providing transdermal patches seatable in the well.

10. The dispenser as in claim 9, further comprising a mechanical conveyor positioned to advance one of the transdermal patches in the supply into the well.

* * * * *